United States Patent [19]

Lysenko et al.

[11] Patent Number: 5,399,768
[45] Date of Patent: Mar. 21, 1995

[54] PROCESS FOR THE PREPARATION OF DIAMINORESORCINOL

[75] Inventors: Zenon Lysenko; Richard G. Pews, both of Midland, Mich.

[73] Assignee: The Dow Chemical Company, Midland, Mich.

[21] Appl. No.: 173,452

[22] Filed: Dec. 23, 1993

[51] Int. Cl.6 .......................................... C07C 209/18
[52] U.S. Cl. ................... 564/418; 564/420; 564/422; 564/423
[58] Field of Search ................... 564/418, 423

[56] References Cited

U.S. PATENT DOCUMENTS

| | | | |
|---|---|---|---|
| 3,862,245 | 1/1975 | Greco | 260/621 M |
| 4,766,244 | 8/1988 | Lysenko | 564/418 |
| 4,962,198 | 10/1990 | Makosza et al. | 544/182 |
| 5,001,265 | 3/1991 | Liu et al. | 564/418 |
| 5,001,279 | 3/1991 | Yin | 568/709 |
| 5,099,057 | 3/1992 | Lysenko | 558/269 |

OTHER PUBLICATIONS

"Hydroxylation of Nitroarenes with Alkyl Hydroperoxide Anions via Vicarious Nucleophilic Substitution of Hydrogen" by Mieczyslaw Makosza et al listed in The Journal of Organic Chemistry vol. 55, No. 17 ©1990 American Chemical Society.

"Preparation of 1,3-dihydroxy-4,6-diaminobenzene as material for poly(benzbisoxazoles" by Sato Tetsuo et al listed in Chemical Abstracts, vol. 112. (1990); 112:157853.

U.S. Patent Office Submitted Application, Filed Dec. 23, 1993, entitled "A Process for the Preparation of Diaminoresorcinol" inventors Zenon Lysenko et al. Attorney Docket No. C-41,706 (Ser. No. 08/173,547).

U.S. Patent Office Submitted Application, Filed Dec. 23, 1993, entitled "A Method of Cleaving Arylethers" inventors Zenon Lysenko et al. Attorney Docket No. C-41,228 (Ser. No. 08/173,451).

"Preparation of 1,3-dihydroxy-4,6-diaminobenzene and its Salts" by Kato Kazufumi et al. listed in Chemical Abstracts vol. 113:152015y (1991).

"Preparation of 1,3-dihydroxy-4,6-diaminobenzene of its Salts as Materials for Poly(benzobisoxazoles" by Kato, Kazufumi et al. listed in Chemical Abstracts vol. 114:121720v (1992).

"Preparation of 4,6-dinitroresorcinol from 1,5-dichloro-2,4-dinitrobenzene" by Rauner Wolfram et al listed in Chemical Abstracts vol. 70:11268q (1944).

Primary Examiner—Glennon H. Hollrah
Assistant Examiner—B. Burn
Attorney, Agent, or Firm—Lynn M. Zettler

[57] ABSTRACT

The present invention relates to a method of preparing 4,6-diaminoresorcinol from 1,2-dichloro-3,5-dinitrobenzene comprising the steps of:

(a) contacting 1,2-dichloro-3,5-dinitrobenzene with a hydroperoxide in the presence of anhydrous base to form 2,3-dichloro-4,6-dinitrophenol;

(b) contacting 2,3-dichloro-4,6-dinitrophenol with a hydroxy-containing compound to form 2-chloro-4,6-dinitroresorcinol; and (c) converting 2-chloro-4,6-dinitroresorcinol to 4,6-diaminoresorcinol, which is isolated as a salt or other stabilized form thereof,

17 Claims, No Drawings

PROCESS FOR THE PREPARATION OF DIAMINORESORCINOL

BACKGROUND OF THE INVENTION

The present invention relates to a method for the preparation of diaminoresorcinol.

4,6-Diaminoresorcinol is a monomer used in preparing polybenzoxazoles (PBO). Although there are a number of known methods for preparing 4,6-diaminoresorcinol, there continues to be a need to find more efficient and cost effective routes to obtain 4,6-diaminoresorcinol.

One known method involves synthesizing the monomer from 1,2,3-trichlorobenzene as described in U.S. Pat. No. 4,766,244 issued to Lysenko. However, 1,2,3-trichlorobenzene has limited availability.

Another method for preparing 4,6-diaminoresorcinol involves treating 1,3-dichloro-4,6-dinitrobenzene with base, to form 4,6-dinitroresorcinol. Although 4,6-dinitroresorcinol may be reduced to form 4,6-diaminoresorcinol, the product recovery is prohibitively low for commercial value.

In yet another method, the appropriate arylether such as di-arylmethoxy-dinitrobenzene can be cleaved to produce 4,6-diaminoresorcinol. U.S. Pat. No. 5,072,053, issued to Blank et al., describes cleaving arylethers by converting di-arylmethoxydinitrobenzenes to 4,6-diaminoresorcinol by catalytic reduction using a platinum metal supported catalyst, which cleaves the diethers and reduces the nitro groups to amines. However, the method also produces toluene as an unwanted by-product which must be removed or converted back to benzyl alcohol for recycle.

Accordingly, it remains highly desirable to provide a method for preparing 4,6-diaminoresorcinol which does not have the foregoing disadvantages.

SUMMARY OF THE INVENTION

The present invention is a method of preparing 4,6-diaminoresorcinol from 1,2-dichloro-3,5-dinitrobenzene comprising the steps of:

(a) contacting 1,2-dichloro-3,5-dinitrobenzene with a hydroperoxide in the presence of anhydrous base to form 2,3-dichloro-4,6-dinitrophenol;

(b) contacting the 2,3-dichloro-4,6-dinitrophenol with an hydroxy-containing compound to form 2-chloro-4,8-dinitroresorcinol; and (c) converting 2-chloro-4,6-dinitroresorcinol to 4,6-diaminoresorcinol, which is isolated as a salt or other stabilized form thereof.

In a preferred embodiment of the present invention the 1,2-dichloro-3,5-dinitrobenzene is contacted with cumene hydroperoxide in the presence of sodium hydroxide such that vicarious substitution occurs, wherein a hydroxy group displaces a hydrogen instead of a chlorine, to form 2,3-dichloro-4,6-dinitrophenol. 2,3-Dichloro-4,6-dinitrophenol is then contacted with sodium hydroxide to form 2-chloro-4,6-dinitroresorcinol. This compound can then be converted by catalytic hydrogenation using hydrogen and a transition metal catalyst to form 4,6-diaminoresorcinol.

The process of the present invention provides an alternative route for producing 4,6-diaminoresorcinol using vicarious substitution.

DETAILED DESCRIPTION OF THE INVENTION

The first step in the method of the present invention comprises contacting 1,2-dichloro-3,5-dinitrobenzene with a hydroperoxide in the presence of a base to form 2,3-dichloro-4,6-dinitrophenol. 1,2-Dichloro-3,5-dinitrobenzene and a method for its preparation is described in Electrophilic Aromatic Substitution, Part 37, *J. Chem. Soc.*, Perkin Trans. 2 (5), pp. 645–50 by Moodie et al. In a preferred method 1,2-dichloro-3,5-dinitrobenzene is first dissolved in a solvent and then contacted with the hydroperoxide. The solvent may be any solvent for 1,2-dichloro-3,5-dinitrobenzene which is also compatible with other solvents, if any, used to dissolve the base, e.g., liquid ammonia and which will not significantly or adversely affect the formation of 2,3-dichloro-4,6-dinitrophenol. Preferred solvents include methylene chloride, dimethoxy methane, tetrahydrofuran, N-methylpyrrolidinone and dimethylformamide. The most preferred solvent is methylene chloride.

The hydroperoxide can be any tertiary alkyl or aralkyl hydroperoxide. The term aralkyl refers to a radical in which an alkyl H atom is substituted by an aryl group. Preferred hydroperoxides are cumene, tert-butyl, and neopentyl hydroperoxides. More preferred are cumene hydroperoxide and tert-butyl hydroperoxide. Most preferred is cumene hydroperoxide.

Bases which can be used in the first step of the method of the present invention include any base which will deprotonate the hydroperoxide to generate the peroxide anion. Preferably, the base is an anhydrous base dissolved in a solvent, e.g., ammonia, and can be any alkali metal alkoxide or alkali metal hydroxide. Preferred bases are potassium t-butoxide, sodium t-butoxide, potassium hydroxide, sodium hydroxide and lithium hydroxide, with the most preferred being sodium hydroxide.

1,2-Dichloro-3,5-dinitrobenzene, the hydroperoxide and base are used in amounts and at conditions sufficient to form 2,3-dichloro-4,6-dinitrophenol. While the relative amounts of the reactants most advantageously used can vary depending on the reaction conditions, it is generally preferable to use at least a stoichiometric amount or up to 1.1 equivalents of hydroperoxide relative to the amount of 1,2-dichloro-3,5-dinitrobenzene. A stoichiometric amount of hydroperoxide refers to the amount of hydroperoxide needed to react with the reactive site of 1,2-dichloro-3,5-dinitrobenzene, without excess, to produce the desired phenol. The amount of base present is preferably in excess of the molar amount of 1,2-dichloro-3,5-dinitrobenzene present. More preferably, the base is employed in an amount between two and five times the molar amount of 1,2-dichloro-3,5-dinitrobenzene. Most preferably, the base is present in a ratio of 5:1 relative to the amount of 1,2-dichloro-3,5-dinitrobenzene.

In a preferred embodiment for making diaminoresorcinol, the base, e.g., sodium hydroxide, is first dissolved in refluxing liquid ammonia in an inert atmosphere. The temperature of refluxing liquid ammonia is dependent upon the pressure and is typically between about −50° C. to about −10° C. Under atmospheric pressure conditions, the refluxing temperature of liquid ammonia is about −33° C. A solution of cumene hydroperoxide and 1,2-dichloro-3,5-dinitrobenzene in methylene chloride is then added to the stirred liquid ammonia reaction mixture at a rate such that the temperature remains at the refluxing temperature. Upon completion of the addition, the ammonia is evaporated and 2,3-dichloro-4,6-dinitrophenol may be isolated by pouring the reaction mixture into excess aqueous hydrochloric acid and extracted with ethyl acetate. Preferably, the 2,3-dichloro-4,6-dinitrophenol product is not isolated or purified, but is directly converted to 4,6-diaminoresorcinol, thus making the production of 4,6-diaminoresorcinol from 1,2-dichloro-3,5-dinitrobenzene a "one pot" process.

The second step of the present invention involves contacting the 2,3-dichloro-4,6-dinitrophenol produced from the first step with additional base to form 2-chloro-4,6-dinitroresorcinol. Preferably the reaction mixture produced from the first step is used directly without isolation or purification. Although the same base may be used as in the first step, it is not required. The base used in the second step of the present invention may be any base which will displace a chlorine and form 2-chloro-4,6-dinitroresorcinol. The preferred bases are alkali metal hydroxides such as potassium hydroxide, sodium hydroxide and lithium hydroxide, with the most preferred being sodium hydroxide.

2,3-Dichloro-4,6-dinitrophenol and base are used in amounts and at conditions sufficient to produce 2-chloro-4,6-dinitroresorcinol. While the relative amounts of 2,3-dichloro-4,6-dinitrophenol and base most advantageously used can vary depending on the reaction conditions and desired conversions, it is generally preferable to use from about 2 to about 6 equivalents, more preferable from about 3 to about 4 equivalents and most preferable about 3 equivalents of base relative to the amount of 2,3-dichloro-4,6-dinitrophenol.

The reaction is preferably conducted at a temperature from about 30° C. to about 140° C., more preferably from about, 60° C. to about 100° C., and most preferably from about 80° C. to about 90° C., with the most preferred temperature being about 85° C.

The time for the reaction to be completed is dependent upon the temperature, pressure and amount of mixing or agitation. In general, the reaction requires between about 1 to about 24 hours for complete conversion. More preferably the reaction is conducted between about 2 and about 12 hours. Most preferably the reaction is completed in approximately 6 hours. Upon completion, the reaction mixture is acidified and crude 2-chloro-4,6-dinitroresorcinol is obtained.

2-Chloro-4,6-dinitroresorcinol is then reduced and recovered most advantageously as a hydrochloride salt of 4,6-diaminoresorcinol as described in U.S. Pat. No. 4,766,244 issued to Lysenko and U.S. Pat. No. 5,001,265 issued to Liu et al., which are both incorporated herein by reference. Any reduction process which will hydrodechlorinate and reduce nitro groups to amino groups can be used in the process of the present invention. It is preferred to catalytically reduce 2-chloro-4,6-dinitroresorcinol using a catalyst selected from the group comprising a transition metal, stannous chloride, or lithium aluminum hydride. Examples of suitable transition metals include nickel, palladium, platinum, ruthenium, rhodium and osmium. In a preferred method, 2-chloro-4,6-dinitroresorcinol is reduced to 4,6-diaminoresorcinol by contacting with a reducing agent, such as hydrogen gas, in the presence of a reduction catalyst, such as palladium on carbon.

The following examples are set forth to illustrate the present invention and should not be construed to limit its scope. In the examples, all parts and percentages are by weight unless otherwise indicated.

EXAMPLES

Example 1

Preparing 2,3-Dichloro-4,6-dinitrophenol From 1,2-Dichloro-3,5-dinitrobenzene:

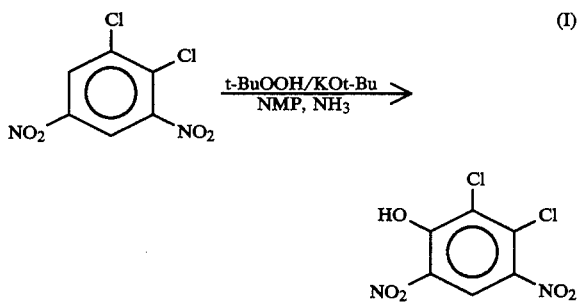

A 100 mL round-bottomed flask with stir bar is charged with 10 milliliters (mL) of liquid ammonia and 5.6 grams (g) (0.050 mol) of potassium t-butoxide. The resulting mixture is refluxed at −33° C. under a dry ice/acetone condenser and a nitrogen atmosphere. A solution of 2.4 g (0.010 mol) 1,2-dichloro-3,5-dinitrobenzene and 1.1 g (1.1 eq.) of 90% t-butyl hydroperoxide in 30 mL of N-methylpyrrolidinone is added dropwise over approximately 1 hour to the agitated refluxing liquid ammonia reaction mixture. Upon completion of the addition, the dry ice/acetone condenser is removed and the ammonia is allowed to evaporate under a stream of dry nitrogen. The crude 2,3-dichloro-4,6-dinitrophenol is isolated by pouring the reaction mixture into 50 mL of aqueous hydrochloric acid, extracted with ethyl acetate and the organic solvents evaporated under reduced pressure (15 mm). The yield of the product is 2.2 g (89%). This product is of sufficient purity to be used without further refinement.

$^1$H NMR (DMSO $d_6$, ppm): 8,677 (s, 1H) $^{13}$C NMR (DMSO $d_6$, ppm): 123,553, 128,885, 130.286, 131,863, 134,766, 157.941.

Example 2

Preparing 2-Chloro-4,6-dinitroresorcinol From 2,3-Dichloro-4,6-dinitrophenol

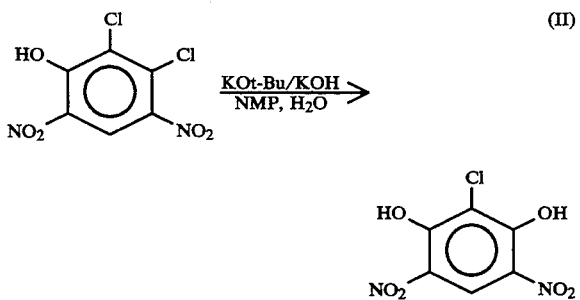

A solution of 2,3-dichloro-4,6-dinitrophenol (2.2 g, 0,008 mol, from previous example), 4.5 g of potassium t-butoxide, 0.4 g of potassium hydroxide, 30 mL of N-methyl pyrrolidinone, and 15 mL of water in a 100 mL round-bottomed flask with stir bar is heated to 85° C. for 6 hours. Upon completion, the reaction mixture is poured into 50 mL of aqueous hydrochloric acid. The resulting product is isolated by filtration, washed with cold water, and air dried. The product is recrystallized from a minimal amount of methanol to yield 1.97 g of 2-chloro-4,6-dinitroresorcinol (95% yield) (85% overall from 1,2-dichloro-3,5-dinitrobenzene).

$^1$H NMR (DMSO d$_6$, ppm): 8,598 (s, 1H); 10.476 (bs, 2H) $^{13}$C NMR (DMSO d$_6$, ppm): 112.192, 122.492, 128.112, 155807.

Example 3

Reduction of 2-Chloro-4,6-dinitroresorcinol to Form 4,6-Diaminoresorcinol Dihydrochloride

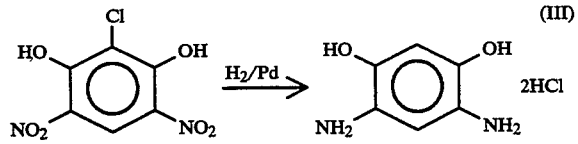
(III)

A 1-L Hastalloy C autoclave, equipped with a gas dispersion turbine, sampling port, thermowell and a cooling coil is charged with 58.6 g (0.25 mole) of 2-chloro-4,6-dinitroresorcinol, 380 g of n-propanol, 100 g of water, and 19.0 g of ammonium acetate. An aqueous slurry of 2.5 g of 10% Pd/C catalyst, is added and the reactor is sealed and purged with nitrogen. Hydrogen gas is charged to the reactor, and the pressure is cycled between 50 and 80 psig while maintaining the temperature of the reaction between 50° C. to 55° C. The progress of the reaction is monitored by hydrogen uptake. When no further hydrogen uptake is observed, the reactor is cooled to room temperature and 300 mL of concentrated HCl, containing 1.5 g stannous chloride dihydrate, is added to the reaction mixture. The resultant product is isolated by filtration and air-dried to yield 57.0 g of crude dihydrochloride salt of 4,6-diaminoresorcinol containing the 10% Pd/C catalyst.

Purification of 4,6-Diaminoresorcinol Dihydrochloride

The crude dihydrochloride salt of 4,6-diaminoresorcinol (57.0 g) containing 10% Pd/C catalyst is dissolved in 400 g of 6% (by weight) aqueous HCl at 80° C. The catalyst present is removed by filtration. An additional 50.0 g of concentrated HCl containing 1.5 g of stannous chloride dihydrate is added to the product mixture along with 5.0 g of activated carbon. The solution is heated at reflux for 15 minutes and the carbon is then removed by filtration. The filtrate is cooled to 0° C. to allow crystallization of the monomer. The resulting precipitate is isolated by filtration under a purge of dry nitrogen. This filter cake is then dried in vacuo at 40° C. to a constant weight to yield 48.7 g of essentially pure (99.8%) 4,6-diaminoresorcinol dihydrochloride having an m.p. of >300° C. with decomposition. Elemental Anal. calc'd for C$_6$H$_{10}$Cl$_2$N$_2$O$_2$ (213.0642): C, 33.82; H, 4.73; Cl, 33.28; N, 13.15; O, 15.02, found: C, 33.6; H, 4.64; N, 13.20.

$^1$H NMR (DMSO d$_6$, ppm): 6.95 (s, 1H); 7.48 (s, 1H); 9.56 (b.s.); 10.5 (b.s.) $^{13}$C NMR (DMSO d$_6$, ppm): 103.69, 109.87, 119.48, 151.25.

What is claimed is:

1. A method of preparing 4,6-diaminoresorcinol from 1,2-dichloro-3,5-dinitrobenzene comprising the steps of:
   (a) contacting 1,2-dichloro-3,5-dinitrobenzene with a hydroperoxide in the presence of anhydrous base to form 2,3-dichloro-4,6-dinitrophenol;
   (b) contacting 2,3-dichloro-4,6-dinitrophenol with an hydroxy containing compound to form 2-chloro-4,6-dinitroresorcinol; and
   (c) hydrogenating 2-chloro-4,6-dinitroresorcinol to 4,6-diaminoresorcinol, which is isolated as a salt or other stabilized form thereof.

2. A method of claim 1 wherein the hydroperoxide is selected from the group consisting of cumene, t-butyl, and neopentyl hydroperoxide.

3. A method of claim 2 wherein the hydroperoxide is cumene hydroperoxide.

4. A method of claim 1 wherein the base used in Step (a) is selected from the group consisting of potassium t-butoxide, sodium t-butoxide, potassium hydroxide, sodium hydroxide and lithium hydroxide.

5. A method of claim 4 wherein the base used in Step (a) is sodium hydroxide.

6. A method of claim 1 wherein the base used in Step (a) and the hydroxy containing compound of Step (b) is sodium hydroxide.

7. A method of claim 1 wherein the base of Step (a) and the hydroxy containing compound of Step (b) are different; the base of Step (a) being selected from the group consisting of potassium t-butoxide, sodium t-butoxide, potassium hydroxide, sodium hydroxide and lithium hydroxide; and the hydroxy-containing compound of step (b) being selected from potassium hydroxide, sodium hydroxide and lithium hydroxide.

8. A method of claim 1 wherein the hydroxy containing compound of Step (b) is selected from the group consisting of potassium hydroxide, sodium hydroxide and lithium hydroxide.

9. A method of claim 8 wherein the hydroxy containing compound of Step (b) is sodium hydroxide.

10. A method of claim 1 wherein step (b) is conducted at a temperature between about 60° C. and about 100° C.

11. A method of claim 10 wherein step (b) is conducted at a temperature between about 80° C. and about 90° C.

12. A method of claim 1 wherein 1,2-dichloro-3,5-dinitrobenzene is first dissolved in a solvent selected from the group consisting of methylene chloride, dimethoxy methane, tetrahydrofuran, and dimethylformamide, before being contacted with the hydroperoxide in the presence of base.

13. A method of claim 12 wherein the solvent is methylene chloride.

14. A method of claim 1 wherein 2-chloro-4,6-dinitroresorcinol is hydrogenated to 4,6-diaminoresorcinol using a hydrogenating agent in the presence of a reduction catalyst.

15. A method of claim 14 wherein the catalyst is nickel, palladium, platinum, ruthenium, rhodium, osmium, stannous chloride, or trialuminum hydride.

16. A method of claim 15 wherein the catalyst is supported and is palladium on carbon.

17. A method of claim 14 wherein the hydrogenating agent is hydrogen gas.

* * * * *